US00RE49254E

(19) United States
(12) Reissued Patent
Nimmagadda et al.

(10) Patent Number: US RE49,254 E
(45) Date of Reissued Patent: Oct. 18, 2022

(54) SYSTEM AND METHOD FOR MASTER DATA MANAGEMENT

(71) Applicant: IQVIA, INC., Parsippany, NJ (US)

(72) Inventors: Prashanth Nimmagadda, Bothwell, WA (US); Stephen Meyles, Seattle, WA (US); Derek Slager, Seattle, WA (US); Drew Vance, Seattle, WA (US); Matthew Ferlo, Seattle, WA (US)

(73) Assignee: IQVIA Inc., Parsippany, NJ (US)

(21) Appl. No.: 17/000,159

(22) Filed: Aug. 21, 2020

Related U.S. Patent Documents

Reissue of:
(64) Patent No.: 10,055,545
Issued: Aug. 21, 2018
Appl. No.: 14/328,047
Filed: Jul. 10, 2014

(51) Int. Cl.

| | |
|---|---|
| ***G06Q 10/06*** | (2012.01) |
| ***G16Z 99/00*** | (2019.01) |
| ***G16H 10/60*** | (2018.01) |
| ***G06F 16/25*** | (2019.01) |
| ***G16H 10/20*** | (2018.01) |
| ***G06F 8/65*** | (2018.01) |
| ***G06F 16/27*** | (2019.01) |

(52) U.S. Cl.
CPC ..... *G06Q 10/06* (2013.01); *G06F 8/65* (2013.01); *G06F 16/25* (2019.01); *G16H 10/20* (2018.01); *G16H 10/60* (2018.01); *G16Z 99/00* (2019.02); *G06F 16/275* (2019.01)

(58) Field of Classification Search
CPC ..... G06Q 10/06; G16H 10/60; G16H 10/20; G16Z 99/00; G06F 16/25; G06F 8/65; G06F 16/275
See application file for complete search history.

(56) References Cited

U.S. PATENT DOCUMENTS 7,788,119 B2 * 8/2010 Najmi ..... G06Q 10/0637 705/7.22
8,041,760 B2 * 10/2011 Mamou ..... G06Q 10/10 709/200
8,606,746 B2 * 12/2013 Yeap ..... G06Q 10/0637 707/694
9,411,864 B2 * 8/2016 Glider ..... G06F 40/151
(Continued)

*Primary Examiner* — Catherine M Tarae
(74) *Attorney, Agent, or Firm* — Fish & Richardson P.C.

(57) ABSTRACT

Some implementations may provide a computer-assisted method for master data management, the method including: receiving configuration information defining a model of entities, each entity encoding attributes of a prescriber of one or more healthcare products; receiving specification information defining mapping logic, searching logic, and matching logic, and merging logic for processing base entities and related entities of the model; receiving data from more than one source customer databases, the customer database including data encoding prescribers of healthcare products and being maintained by more than one organizations; translating the received data into staging data according to the mapping logic in the received specification information; generating master data by processing the staging data according to the searching logic, matching logic, and merging logic in the received specification information; and synchronizing at least a portion of the master data to at least one of the source customer databases.

21 Claims, 6 Drawing Sheets

(56) References Cited

U.S. PATENT DOCUMENTS

| | | | | |
|---|---|---|---|---|
| 9,898,703 | B2 * | 2/2018 | Carriere | G06Q 10/06 |
| 10,216,814 | B2 * | 2/2019 | Allan | G06F 16/254 |
| 10,325,272 | B2 * | 6/2019 | Hunt | G06Q 30/0201 |
| 2008/0244008 | A1 * | 10/2008 | Wilkinson | G06F 17/30545 709/205 |

* cited by examiner

SYSTEM AND METHOD FOR MASTER DATA MANAGEMENT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS REFERENCE TO RELATED APPLICATIONS*

*This application is a reissue application of U.S. Pat. No. 10,055,545, granted Aug. 21, 2018, which issued from U.S. application Ser. No. 14/328,047 filed Jul. 10, 2014.*

BACKGROUND

Healthcare data may be stored in electronic format on diverse database systems by a variety of organizations.

OVERVIEW

In one aspect, some implementations provide as a computer-assisted method for master data management, the method including: receiving configuration information defining a model of entities, each entity encoding attributes of a prescriber of one or more healthcare products; receiving specification information defining mapping logic, searching logic, and matching logic, and merging logic for processing base entities and related entities of the model; receiving data from more than one source customer databases, the customer database including data encoding prescribers of healthcare products and being maintained by more than one organizations; translating the received data into staging data according to the mapping logic in the received specification information; generating master data by processing the staging data according to the mapping, searching logic, matching logic, and merging logic in the received specification information; and synchronizing at least a portion of the master data to at least one of the source customer databases. Within this disclosure, a prescriber may generally include a prescribing doctor, a prescribing nurse, a prescribing minute clinic staff member, a prescribing hospital, a prescribing clinic. Within the disclosure, a database may generally refer to any set of data, and not limited to any particular commercial (nor non-commercial) databases.

Implementations may include one of more of the following features. Processing the staging data may include: based on the searching logic and matching logic in the received specification information, identifying staging data to be processed that encodes a particular prescriber. Identifying staging data that encodes the prescriber may further include: generating a matching score for the identified staging data based on the matching logic. Generating a matching score may further include: weighing and combining contributions of matching attributes of the prescriber as encoded by the identified staging data.

Identifying staging data encoding the prescriber may further include: identifying multiple instances of staging data corresponding to the particular prescriber. The method may further include ranking the identified instances of staging data according to the corresponding matching scores. The method may additionally include: identifying duplicate instances of staging data encoding the same prescriber. The method may further include identifying less updated instances encoding the same prescriber; and pruning the identified less updated instances.

Processing the staging data may further include flagging the identified instances of staging data to an operator. The method may further include receiving operator feedback to prune an identified instance. The method may further include receiving operator feedback that chooses an identified instance as a unique instance encoding the particular prescriber.

Synchronizing at least a portion of the master data may include synchronizing at least a portion of the master data to a source customer database for which the generated master data to prescriber that is inconsistent with data in the source customer systems, database that encodes the same prescriber.

The model of entities may include base entities and related entities, and wherein translating the data into staging data may include: incorporating the received mapping logic into an extraction, transformation, and loading (ETL) layer between the more than one customer database and the staging data, the ETL configured to map at least one related entity via a many to one mapping to related base entities. Mapping could include one-to-one, one-to-many and many-to-one type of mappings.

Translating the data into staging data may include: converting data encoding a prescriber of healthcare products from one entity in a customer database to another entity under the received data model.

The method may further include receiving configuration information in an extendable mark-up language. Receiving data may include: receiving data from a customer relationship management (CRM) database. Receiving data may include: receiving data from an enterprise relationship management (ERM) database.

In another aspect, some implementation may provide a computer system comprising a logical processor and at least one memory, the processor is configured to perform the operations of: receiving configuration information defining a model of entities including base entities and related entities, each base entity relating to one or more related entities, both base entity and related entity encoding an attribute of prescribers of healthcare products; receiving specification information defining mapping logic, searching logic, and matching logic for processing base entities and related entities of the model; receiving data from more than one customer database, the customer database including data encoding prescribers of healthcare products and being maintained by more than one organizations; translating the received data into staging data according to the mapping logic in the received specification information; generating master data by processing the staging data according to the searching logic and matching logic in the received specification information; and synchronizing at least a portion of the master data to at least one customer database.

Implementations may include one or more of the following features. Processing the staging data may include: based on the searching logic and matching logic in the received specification information, identifying staging data that encodes a prescriber.

Synchronizing at least a portion of the master data may include synchronizing at least a portion of the master data to a source customer system for which the generated master data includes data encoding a prescriber that is inconsistent with data in the customer database that encodes the same prescriber.

Translating the data into staging data may include: incorporating the received mapping logic into an extraction, transformation, and loading (ETL) layer between the more than one customer database and the staging data. Translating the data into staging data may include: converting data encoding a prescriber of healthcare products from one entity in a customer database to another entity under the received data model.

The operations may further include receiving configuration information in an extendable mark-up language. Receiving data may include: receiving data from customer relationship management (CRM) database. Receiving data may include: receiving data from an enterprise relationship management (ERM) database.

In yet another aspect, some implementations provide a computer-readable medium comprising software instructions that, when executed by a processor of a computer, cause the processor to perform the operations of: receiving configuration information defining a model of entities including base entities and related entities, each base entity relating to one or more related entities, both base entity and related entity encoding an attribute of prescribers of healthcare products; receiving specification information defining mapping logic, searching logic, and matching logic for processing base entities and related entities of the model; receiving data from more than one customer database, the customer database including data encoding prescribers of healthcare products and being maintained by more than one organizations; translating the received data into staging data according to the mapping logic in the received specification information; generating master data by processing the staging data according to the searching logic and matching logic in the received specification information; and synchronizing at least a portion of the master data to at least one customer database.

Implementations of the above techniques include a method, computer program product and a system. The computer program product is suitably embodied in a non-transitory machine-readable medium and includes instructions executable by one or more processors. The instructions are configured to cause the one or more processors to perform the above described actions.

The system includes one or more processors and instructions embedded in a non-transitory machine-readable medium that are executable by the one or more processors. The instructions, when executed, are configured to cause the one or more processors to perform the above described actions. The default position is not to use any external databases, but the system could be configured to perform a database check if needed.

The details of one or more aspects of the subject matter described in this specification are set forth in the accompanying drawings and the description below. Other features, aspects, and advantages of the subject matter will become apparent from the description, the drawings, and the claims.

DETAILED DESCRIPTION

Figure 1:
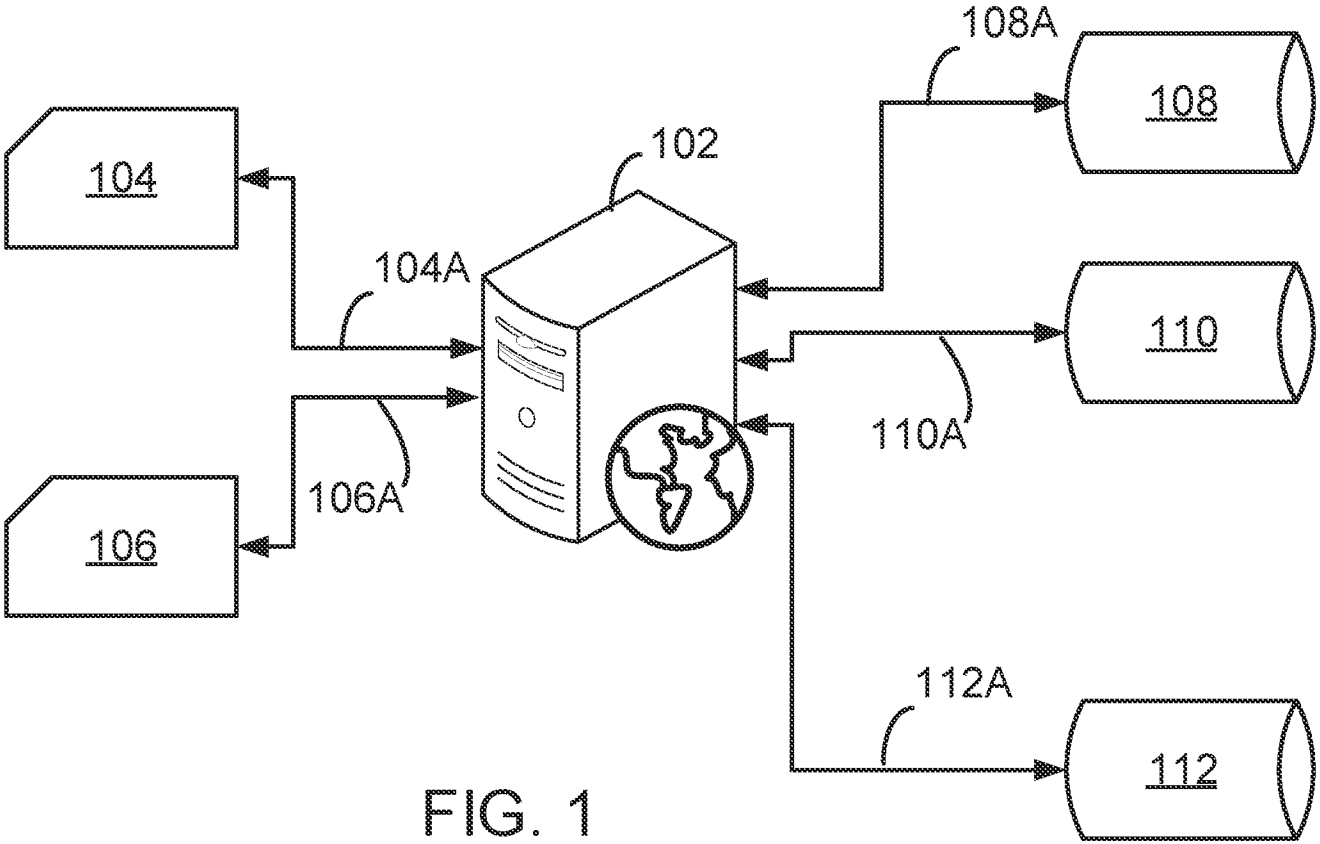
FIG. 1 illustrates an example situation in which master data is stored on a multitude of data storage systems.

This disclosure generally describes systems and methods for managing master data stored on a multitude of disparate database systems. Implementations disclosed herein incorporate a configuration framework through which a data manager can configure, for example, models for data entities, relationship of modeled entities of master data, and rules for mapping, searching, matching, and merging the modeled entities of master data. Software tools disclosed herein allow easy configuration of associated properties of each modeled entity, relationships between these data entities, as well as intuitive visualization of data entities. The framework allows data managers to consolidate different versions of the same master data stored at a multitude of departments or organizations. In particular, the framework allows for a single point configuration for all stages of data lifecycle from ingesting data from client systems, creating master data records, and finally publishing master data records back to client systems for end to end synchronization. System and method disclosed herein may allow for ease of master data maintenance. Such master data is extensible over time. Moreover, system and method include processing components that sanitize and display the data on a browser for ease of use. Within the disclosure, a database may generally refer to any set of data, and not limited to any particular commercial (nor non-commercial) databases.

Healthcare database may serve a central role in healthcare, including patient care, administration, research and education. Healthcare data may generally refer to the healthcare records of a patient generated by a multitude of institutions, including for example, primary care physicians, hospitals, clinics, pharmacy stores, etc. These institutions may span across the country, or even the world. Such healthcare data is becoming increasingly more and more electronic. As an illustration, picture archiving and communication system (PACS) may manage imaging data of a patient obtained at a radiology or cardiology department of a hospital. Generally, diagnostic test results, history of taking drugs for treatment, surgery history, or even family history and genetic predisposition can all become part of the healthcare data of a patient. Such healthcare data in electronic form may provide patients and treating physicians with easy access to relevant healthcare data. As another illustration, insurance transactions may be conducted electronically. In fact, to provide faster service and easier access, more and more insurance companies are processing insurance claims and disbursing funds electronically.

To provide quality of service, healthcare database is expected to function across the boundaries of different institutions and technologies. These electronic databases may be hosted by different institutions anywhere in the country or even across borders. Examples of data storage technologies that are use in healthcare databases may include, but are not limited to, SQL (structured query language) data servers, non-SQL data servers, network attached storage (NAS) servers, direct attached storage (DAS) device, storage area network (SAN) storage, etc. Example data storage technologies may also include cloud storage through which electronic healthcare data may be stored in virtualized pools of storages managed by third parties.

For context, healthcare data, in electronic form, is growing larger in size facilitated by hardware improvements in speed and capacity of mass storage devices, as well as similar advances in processor and networking speed. Healthcare databases may be partitioned in large tables across a cluster of separate database servers with diverse storage technologies. For example, network-attached storage (NAS) and storage area networks (SANs) coupled with fast local area networks and Fibre Channel technology enable still larger, more loosely coupled configurations of databases and distributed computing power. Example implementations of distributed database storage may include X/Open XA standard and Oracle RACrelies, both of which employs high-speed network connections between data storage servers. In the context of describing data storage technologies, server, system, and device may be used interchangeably.

In the context of electronic healthcare data, master data represents the business objects which are agreed on and shared across a healthcare enterprises, such as a healthcare provider. In one example, master data is a single source of basic business data used across multiple systems, applications, and/or processes. In another example, master data refers to the single source of basic business data used across all systems, applications, and processes for an entire healthcare enterprise (all departments, divisions, companies, and countries). While it is often non-transactional in nature, master data is not limited to non-transactional data, and often supports transactional processes and operations. For example, master data may include information about patients, doctors, products, materials, suppliers, and vendors, but may also cover services, records, and documents. Analysis and reporting of our healthcare record is greatly dependent on the quality of an organization's master data. Master data may either be stored in a central repository, sourced from one or more systems, or referenced centrally using an index. However, when it is used by several functional groups it may be distributed and stored in different applications across an organization and this copy data may be inconsistent (and if so, inaccurate).

In one example, after receiving a treatment at a hospital, the patient incurs an expense for consuming a prescribed healthcare product. The hospital's financial department immediately contacts the patient's insurance carrier for insurance payment according to its own customer relationship management (CRM) database. This department's CRM database may reflect a healthcare insurance carrier captured from the patient on his initial visit, which may not be the same as the current one as reported by the patient to the clinic department during the patient's most recent visit. As a business matter, each healthcare insurance carrier may have implemented variable procedures depending on, for example, the manufacturer of an implant, the supplier of a sedative, the amount of deductibles. The procedures may require different billing codes for expenses incurred during the same procedure on the same day. The financial department may inadvertently have entered the billing code for the various expenses incurred during the procedure, assuming that the patient is still with the initial healthcare insurance carrier. As a result, the reimbursement is bounced, which triggers an alert at the billing department. While the financial department remedies the inadvertent error by renewing its reimbursement request at the current healthcare insurance carrier (after getting to the bottom of the issue), the billing department is unaware of such efforts on part of the financial department. Assuming that the patient does not have insurance coverage for the treatment received, the billing department issues an invoice to the patient. When the patient receives the bill, the patient may be surprised and shocked. To investigate the issue, the patient may be calling the insurance carrier, who may tell the patient that the procedure is covered and a payment is being made to the hospital. Upon hearing such communication, the patient may get upset and may initiate further communications with the treating physician at the hospital. Such events can become a customer relation nightmare for the hospital. Similar glitches may occur at insurance carriers when master data at various departments are segmented and inconsistent.

In another example, a prescriber is initially affiliated with a first local clinic. The prescriber can be a treating physician, a nutritionist, a physical therapist, a nurse. Depending on the context and local regulations, the prescriber can prescribe a healthcare product, such as a prescription pharmaceutical product or a prescription therapeutic device. A database of local practitioners may include the prescriber as a likely candidate to receive marketing materials fin healthcare products within the specialty of the prescriber. The database may be maintained by a customer relationship management (CRM) entity. In some instances, the CRM entity can be a subsidiary organization of a healthcare product manufacturer (e.g., a pharmaceutical company). In other instances, the CRM entity can be a third party organization. To further develop the prescriber's practice, the prescriber moves to a second local clinic that offers more growth potential in patient patronage. In some cases, a record entry showing the prescriber's new affiliation may be entered into the database run by the CRM entity. Yet, the record entry showing the prescriber's initial affiliation with the first clinic may persist. Thus, duplicate entries for the same prescriber may exist in the database maintained by the CRM entity. The problem may be exacerbated by mergers and acquisitions of local clinics. The duplicate entries may provide inconsistent contact information of healthcare providers. The potential inconsistency may lead to wasted marketing efforts as sales staff visit the prescriber at an out dated office address, materials sent to the prescriber at an out dated mailing address, and voicemails left at out dated phone numbers. Within this disclosure, a prescriber may generally include a prescribing doctor, a prescribing nurse, a prescribing minute clinic staff member, a prescribing hospital, a prescribing clinic.

Master data management seeks to ensure an organization, such as a CRM management entity, does not use multiple (potentially inconsistent) versions of the same master data in various departments of the same organization. MDM also addresses the quality of data, consistent classification and identification of data, and data-reconciliation issues. Master data management of disparate data systems requires data transformations as the data extracted from the disparate source data system is transformed and loaded into the master data management hub. To synchronize the disparate source master data, the managed master data extracted from the master data management hub is again transformed and loaded into the disparate source data system as the master data is updated. As with other Extraction, Transformation, and Loading (ETL)-based data movement, these processes are expensive and inefficient to develop and to maintain which greatly reduces the return on investment for the master data management product.

One common reason for some large corporations to experience massive issues with MDM is growth through mergers or acquisitions. Two organizations which merge will typically create an entity with duplicate master data (since each likely had at least one master database of its own prior to the merger). Ideally, database administrators resolve this problem through de-duplication of the master data as part of the merger. In practice, however, reconciling several master data systems can present difficulties because of the dependencies that existing applications have on the master databases. As a result, more often than not the two systems do not fully merge, but remain separate, with a special reconciliation process defined that ensures consistency between the data stored in the two systems. Over time, however, as further mergers and acquisitions occur, the problem multiplies, more and more master databases appear, and data-reconciliation processes become extremely complex, and consequently unmanageable and unreliable. Because of this trend, one can find organizations with 10, 15, or even as many as 100 separate, poorly integrated master databases, which can cause serious operational problems in the areas of customer satisfaction, operational efficiency, decision-support, and regulatory compliance. As our healthcare system is growing increasingly dependent on data, in a digital form and subject to onerous regulations, master data management is an major consider for the healthcare industry.

FIG. 1 is a diagram showing an example computer system 102 for running master data management (MDM) coupled to databases 104 and 106 as well as data storage systems 108 to 112. Computer system 102 may be any computer or computing apparatus consistent with the description herein. Computer system 102 may be receive database data from to various sources including databases 104 and 106 as well as data storage systems 108 to 112.

Database 104 and 106 may include customer relation management database containing information of primary care physicians, treating physicians, physical therapists, or insurance providers. Database 104 and 106 may include enterprise relation management database containing information of hospitals, clinics, out-patient centers, counseling centers, or organizations authorized to prescribe healthcare products (e.g., medicine, devices, disposables, etc.). The databases may communicate with MDM computer 102 via logic connections 104A and 106A. Data may be downloaded from the databases or uploaded to the databases via logic connections 104A and 106A.

The databases may be hosted on a variety of data storages 108 to 112. The data storages may include hard disk drives, Flash drives, redundant array of inexpensive disks (RAID), RAID arrays, hybrid disks including both hard disk drives and Flash drives. The data storage devices may be managed by various software implementations to tailor performance metrics including latency and throughput to the specific context of a database application. The storage devices may be placed on a variety of communications networks including wired and wireless networks. As illustrated, the storage devices may communicate with MDM server computer 102 via physical communications 108A, 110A, and 112A.

Figure 2:
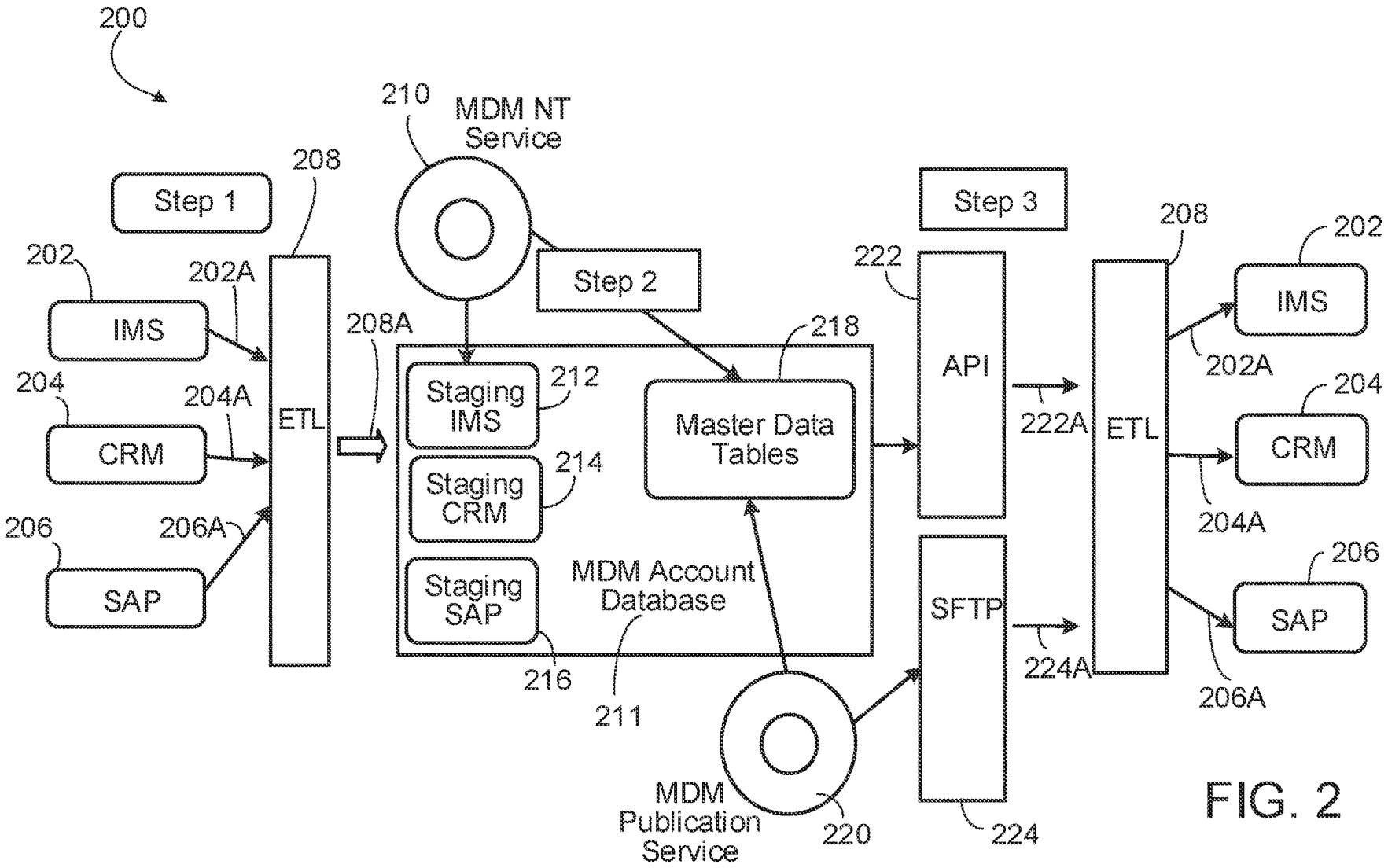
FIG. 2 is a diagram an example system for managing master data front a multitude of sources.

FIG. 2 is a diagram showing an architecture of master data management according to some implementations. As illustrated, in step 1, database data including CRM data can be obtained from various databases 202 to 206. An extract, transform, and load (ETL) layer may be configured to bring database data from the customer databases into the staging area. During step 2, staging data 212 to 216 may be processed by search/match and merge logic to generate master data schema within the MDM account of a subscribing user. The subscribing user may include, for example, a pharmaceutical company, the marketing subsidiary of a pharmaceutical company, a medical device company, the marketing subsidiary of a medical device company, an insurance carrier, the marketing subsidiary of an insurance carrier. Each subscribing user may have a subscriber account maintained at MDM server 102. Each subscriber account is configured with search/match and merge rules based on the data model of the subscribing user. In some implementations, extensible mark-up language (XML) may be chosen to represent the configuration rules and data model. In other implementations, other extensible programming languages such as JSON may be used for the representation schemes. A MDM publication service 220 may be configured to publish the generated master data schema and synchronize the master data to respective databases 202 to 206.

In some implementations, the data model of a subscribing user may be generated by human analysts. For example, a consulting analyst may visit the site of the subscribing user to discuss the specific needs and requirements of the subscribing user. In some cases, the needs and requirements of the subscribing user may depend on the ERM and CRM databases accessible to the subscribing user as well as the marketing initiative and history of the subscribing user. To address the specific needs and requirements of the subscribing user, the consulting analyst may draft a master data model for the subscribing user. The master data model may specify entities and their mapping relationships. Entities can include base entities and related entities. Base entity may be the foundation entity in the data model and each related entity is related to one or more base entities. Example configurations for base entities and related entities are listed below in extendable mark-up language (XML).

TABLE 1

```
<datamodel id="mdm" >
  <baseentity id="Contact">
    <relatedentity id="MdmContactAddress" />
    <relatedentity id="MdmContactCommunication" />
    <relatedentity id="MdmContactSpeciality" />
    <relatedentity id="MdmContactLicense" />
    <relatedentity id="MdmContactIdentifier" />
  </baseentity>
  <baseentity id="Facility">
    <relatedentity id="FacilityClassOfTrade" />
    <relatedentity id="FacilityClassification" />
    <relatedentity id="FacilityIdentifier" />
  </baseentity>
  <baseentity id="ContactFacility" />
  <baseentity id="FacilityToFacility" />
</datamodel>
```

Table 1 shows three base entities in a data model, namely contact, facility, contact facility, and facility to facility. The contact base entity has five related entities, including, address, communication, specialty, license, and identifier. The facility base entity includes three related entities, including class of trade, classification, and identifier. The example is provided solely for illustration purpose. Although the example is written in XML, other language can be used without deviating from the purpose and spirit of the disclosure. In the above example, when a base entity has no related entity, such base entity may become a base entity on its own.

As illustrated in FIG. 2, a variety of databases may be accessible to the subscribing user, including an IMS proprietary database 202, a customer relation management (CRM) database 204, and an enterprise relation management (ERM) database 206. By way of illustration only, IMS proprietary database 202 may be maintained exclusively by IMS health services. In one instance, CRM database 204 is a database maintained by subscribing user internally. In another instance, CRM database 204 is a database maintained by a third-party but accessible to subscribing user, for example, on a fee-for-service basis. Similarly, ERM database 206 can be a database maintained by subscribing user internally. ERM database 206 can also be a database maintained by a third-party but accessible to subscribing user, for example, on a fee-for-service basis. Databases 202, 204, and 206 may interact with MDM server 102 through ETL layer 208 via logic connections 202A, 204A, and 206A respectively. The logic connections may include, for example, software sockets over transmission control protocol/internet protocol (TCP/IP).

The ETL layer 208 is configured to bring in database data from a variety of accessible databases into the MDM account database 211. In some implementations, the ETL layer is a software wrapper of the disclosed master data management process for interfacing with data warehousing applications (including customer databases). In other implementations, the ETL layer is a separate process/daemon for interfacing between source databases and master data management processes as disclosed herein.

For ETL 208 to read database data into MDM account database, a configuration file may be prepared by the consulting analyst. The configuration file may list configuration information specifying the data model of entities in the staging area. Example configurations for staging entities are listed below in extendable mark-up language (XML).

TABLE 2

```
<datamodel id="ims" >
<baseentity id="HCPProfile">
    <relatedentity id="ImsMasterAddress" />
    <relatedentity id="PrescriberAddress" />
```

TABLE 2-continued

```
    <relatedentity id="HCPSpeciality" />
    <relatedentity id="HCPLicense" />
    <relatedentity id="HCPIdentifier" />
  </baseentity>
  <baseentity id="HCOBusiness">
    <relatedentity id="HCOClassOfTrade" />
    <relatedentity id="HCOBusinessClassOfTrade" />
    <relatedentity id="HCOBusinessIdentifier" />
  </baseentity>
  <baseentity id="HCOBusinessToProfessional" />
  <baseentity id="HCOBusinessToBusiness" />
</datamodel>
```

Table 2 shows an example data model of staging IMS HCPS and HCO entities. The data model includes four base entities, namely HCPPrfile, HCO business, HCOBusinessToProfessional, and HCOBusinessToBusiness. The HCPPrfile base entity has five related entities, including, ims master address, prescriber address, specialty, license, and identifier. The HCP business base entity includes three related entities, including class of trade, classification, and identifier. The example is provided solely for illustration purpose. Although the example is written in XML, other language can be used without deviating from the purpose and spirit of the disclosure.

In addition, the consulting analyst may prepare the mapping from an entity in the source database to an entity in the MDM staging area. Example configurations for mapping from one entity to another are listed below in extendable mark-up language (XML).

TABLE 3

```
<entitymap from="HCPProfile" to="Contact">
  <crossreference>
    <field id="IMSId" />
  <crossreference>
  <mapgroup>
    <onetoone>
      <fieldmap from="IMSId" to="ImsContactId"/>
      <fieldmap from="Prefix" to="Salutation"/>
      <fieldmap from="FirstName" to="FirstName"/>
      <fieldmap from="MiddleName" to="MiddleName"/>
      <fieldmap from="LastName" to="LastName"/>
      <fieldmap from="Suffix" to="GenerationalSuffix"/>
      <fieldmap from="FormerName" to="FormerName"/>
      <fieldmap from="MaidenName" to="MaidenName"/>
      <fieldmap from="Gender" to="Gender" />
      <fieldmap from="GenderDescription" to="GenderDescription" />
      <fieldmap from="AmaPdrpEffectiveDate" to="AmaPdrpEffectiveDate"/>
      <fieldmap from="HcProfStatusCode" to="HcProfStatusCode"/>
      <fieldmap from="HcProfStatusDesc" to="HcProfStatusDesc"/>
      <fieldmap from="BirthYear" to="BirthYear"/>
      <fieldmap from="GradDate" to="GradDate"/>
      <fieldmap from="GradMedicalTrainingDesc" to="GradMedicalTrainingDesc"/>
      <fieldmap from="AmaPdrpIndicator" to="AmaPdrpIndicator"/>
      <fieldmap from="Deleted" to="Deleted"/>
      <fieldmap from="XRefIMSId" to="XRefIMSId"/>
      <fieldmap from="IsCustomerOwned" to="IsCustomerOwned"/>
      <fieldlabel from="IMS" to="ExtSourceSystem" />
    </onetoone>
  </mapgroup>
</entitymap>
```

Table 3 shows an example one-to-one mapping between base entities HCPProfile and Contact. The one-to-one mapping shows the corresponding attributes for each entity. The example mapping defines how to transform and convert data from one entity to another entity. In some implementations, multiple mappings may be provided to enable multiple steps of transformation/conversion in series. The example is provided solely for illustration purpose. Although the example is written in XML, other language can be used without deviating from the purpose and spirit of the disclosure.

The example configuration information may indicate how entities should be related to each other in terms of keys, and relationship cardinality (for example, 1:1, 1:m, m:m). For context, the cardinality of one data table with respect to another data table correspond to relationships between data tables, i.e., explaining how each table links to another. In the relational database model, tables can be related as any of: many-to-many, one-to-many, or one-to-one. This mapping may be deemed the cardinality of a given table in relation to another. For example, consider a database designed to keep track of hospital records. Such a database could have many tables like: a Doctor table full of doctor information, a Patient table with patient information, and a Department table with an entry for each department of the hospital. In this hypothetical model: a many-to-many relationship exists between the records in the Doctor table and records in the Patient table (Doctors have many patients, and a patient could have several doctors); a one-to-many relation exists between the Department table and the Doctor table (each doctor works for one department, but one department could have many doctors). In this hypothetical model, a one-to-one relationship may exist if, for example, the Doctor's table is split in two to keep apart doctors' personal or administrative information. In data modeling, collections of data elements are grouped into data tables. The data tables contain groups of data field names (also known as database attributes). Data tables are linked by key fields. A primary key assigns that field's special order to a table. In this hypothetical mode, a primary key for the doctor's table may be the attribute of DoctorID. A table can also have a foreign key which indicates that that field is linked to the primary key of another table. A complex data model can involve hundreds of related tables, which may be stored across various institutions and different storage systems.

After database data has been read by ETL layer 208 into MDM account database, the source database data may be transformed and converted into staging data. As illustrated in FIG. 2, source database data from IMS database 202, CRM database 204, SAP database 206 may be transformed and converted into staging IMS data 212, staging CRM data 214, and staging SAP data 216. The transformed data may be loaded via logic connection 208A into master account database 211. In the illustrated example, MDM NT service runs core search/match and merge logic to verify and consolidate data from various source systems into master data schema. In one instance, the MDM NT Service is a common shared Windows service. The Windows service may isolate processing per account or data source or per staging data. The isolation may be realized in a multi-thread implementation. The Windows service may also parallelize searching/matching using multi-thread implementations to improve throughput or reduce latency. In other instances, the MDM service may incorporate a Linux or Unix process to isolate processing per account/data source and parallelize execution for improve throughput or latency.

The search and match may be specified by additional configurations. The following Table 4 shows an example search logic.

TABLE 4

```
<mdmsearch id="Contact.Default" combiningfunction="Intersection">
  <bucket>
    <field typeid="Contact" fieldid="Gender" />
  </bucket>
  <bucket>
    <field typeid="MdmContactAddress" fieldid="Zip5" />
  </bucket>
  <bucket>
    <substring startindex="0" length="3">
      <field typeid="Contact" fieldid="FirstName" />
    </substring>
    <field typeid="Contact" fieldid="LastName" />
  </bucket>
</mdmsearch>
```

The example Mdmsearch configuration shown in Table 4 allows an optimized collection of search groups that can be combined via an Intersection or Union or IntersectionOrUnion combinations. Here, an intersection implies search that matches all conditions (thereby referring to data common to all search groups); a union implies all the results aggregated into a collection (thereby referring to data from all search groups); and an intersectionOrUnion implies preference being given to common search results, and if not found get all matched data. In this specific example, an intersection may be performed on 3 groups, namely, Gender, Zip5 and, LastName+First-3-characters of FirstName. Since this is an intersection type of search configuration, only master data for matching that meets all these criteria may be fetched. With expandable configuration rules to specify search logic, structured and context aware search criteria can be constructed based on entire data model. Moreover, cross-reference searches as configured in entityMap may enable directly lookup of master data from a given data source record for faster performance.

Additionally, some implementations may incorporate join operations, the "entityjoins" configuration sections may be programmed to compile the proper joins. For context, a join operation in database management merges data entities from two or more tables. Example joins may be include: cross join, which combine each row from the first table with each row of the second table by concatenating rows from both tables; inner joins, which combines rows from the first table with rows from the second table based a join-predicate, for example, when fields from rows in both tables have common values; outer joins, which does not require each record in the two joined tables to have to a matching value. Other joins may be defined by, for example, the American National Standards Institute (ANSI) standards or a particular vendor. The "entityjoins" configuration may specify the join operations supported by a particular underlying data storage system. An application programmer, however, may not need to implement any join operations in the application program code being developed.

Besides searching logic, the configuration information also includes matching logic. The following Table 5 shows an example match logic.

TABLE 5

```
<mdmmatch id="Contact.Default" threshold="5"
possiblethreshold="2">
  <matchrule matchruletype="Simple" matchscore="1"
```

TABLE 5-continued

```
comparison="Equals">
  <field typeid="Contact" fieldid="LastName" />
</matchrule>
<matchrule matchruletype="Simple" matchscore="1"
comparison="Equals">
  <field typeid="Contact" fieldid="FirstName" />
</matchrule>
<matchrule matchruletype="Simple" matchscore="1"
comparison="Equals">
  <field typeid="Contact" fieldid="MiddleName" />
</matchrule>
<matchrule matchruletype="Simple" matchscore="1"
comparison="Equals">
  <field typeid="Contact" fieldid="Gender" />
</matchrule>
<matchrule matchruletype="Simple" matchscore="1"
comparison="Equals">
  <field typeid="MdmContactSpeciality"
  fieldid="SpecCode" />
</matchrule>
</mdmmatch>
```

In this example mdmmatch configuration may enable the creation of a context aware score based on match criteria. The matching score can allow the MDM service 210 to rank the degree of match for multiple entities. The degree of match can be quantified based on contributions of each matching attribute. A particular matching attribute may be given a score. The matching score of an entity is then the summation of contributions from all matching attributes. In the above example, a matching last name, a matching first name, a matching middle name, a matching gender, a matching specialty is each given a score of 1. In the above example, matching is defined as a comparison of "Equals."

In the above example, a threshold of matching score may be defined. Specifically, a customer can configure two metrics for Threshold, namely, PossibleThreshold and Threshold number. Possible Threshold indicates the score number above which an inbound entity should be treated as a potential match of one or more existing record. Threshold number indicates the ceiling score number, indicating any value higher than this indicates a duplicate of existing golden entities. An existing golden entity is an entity identified as a trusted entity whose quality and freshness have been verified. Moreover, the matching logic can be extensible with the configuration examples. For instance, the contribution from each matching attribute may be equal or dependent on a distance factor.

In addition to searching and matching logic, the configuration information also includes merge logic. The following Table 6 shows an example merge logic.

TABLE 6

```
<mdmmerge id="MdmContactAddress">
  <idfield id="Line1" />
  <idfield id="Line2" />
  <idfield id="City" />
  <idfield id="State" />
  <idfield id="Zip5" />
  <field id="ImsAddressId">
    <sourcepriority>
      <source name="IMS" priority="100" />
    </sourcepriority>
  </field>
  <field id="*" ignorenull="false">
    <sourcepriority>
      <source name="MS" priority=" 10" />
      <source name="CRM" priority="5" />
```

TABLE 6-continued

```
    </sourcepriority>
  </field>
</mdmmerge>
```

The above example MdmMerge configurations inform the system as to how to merge two entities of same type together. In this example configuration, the <idfield> tag allows for an entity to have one or more composite-keys to complement their current primary keys in the persistent store. During merge scenarios when an inbound entity (e.g., an entity encoded in database data from a source database) is not yet persisted, the primary keys of the inbound entity will be NULL and cannot be compared with existing data. In these scenarios using a composite-key based on the <idfield> tag may allow a comparison of two entities together. Nonetheless, this example also allows two entities in persistent store to be merged together.

The example configuration additionally specifies the priority metric for each source database. In other words, the source databases may not be treated equally because some source databases may be better maintained or more authoritative than others. In the example above, IMS database is treated more favorably than a CRM database. Hence, each entity can also define a default precedence rule based on the data sources, while maintaining an override at field by field for improved flexibility.

MDM service 210 may process staging data 212 to 216 based on the search, match, and merge logic, the example configurations of which are listed above. Depending on the match score the inbound record from data source is deemed unique, duplicate or a potential match of one or more existing record. Unique instances of an entity may be identified and kept. Specifically, unique records are inserted into persistence system and become master data from that point forward. Duplicate instances of an entity may also be identified and merged into a master record. For example, instances of the same prescribing doctor may be merged into one master record with the most updated contact information or affiliation information of the prescribing doctor. MDM service 210 may process duplicate records via Merge logic (as illustrated in the example above), by applying merge rules to dictate data source precedence for attribute level survivorship. In addition, MDM service 210 also maintains cross references to source customer databases, to the extent that data entries for a prescriber may exist in various source customer databases.

In some implementations, potential matches may be stored as temporary unique records, and they are queued up in a "GrayMatch" task queue. In some implementations, human interventions may be required to determine whether the potential matches in the graymatch task queue. This human intervention can be done by a consulting analyst via an interface called "DataSteward." Datastewards are provided as an interface, for example, a browser based window, to records that are potential matches along with their match candidates. Datastewards can allow the consulting analyst to compare two master records and establish whether these records are similar or different. If the potential matches are identified as similar, Datasteward can also trigger the "Merge" processing logic.

In addition to the data curation, a subscribing user can choose to send full and delta data publish of master data on a recurring time interval. In one example, MDM Publication Service 220 is a windows service that writes the contents of system of record into flat files, and uploads them into a secure share. For a delta publish, MDM publication service 220 will publish records that have been modified since the last time publish has been processed and output the delta. In another example, the MDM publication service 220 may incorporate a Linux or Unix process writes the contents of system of record into fiat files, and uploads them into a secure share.

In some implementations, the publication may be through application program interface (API) 222. For example, the MDM account database may include an API to enable master data to be exported via logic connection 222A and through ETL layer 208 to source databases, including, IMS database 202, CRM database 204, and SAP database 206.

In other implementations, MDM publication service 220 may cause the master data to be transferred via a secure file transfer protocol (SFTP) 224. As illustrated, the SFTP approach is through ETL 208 and via logic connection 224A. The SFTP approach may transfer master data to source databases, including, IMS database 202, CRM database 204, and SAP database 206.

Implementations disclosed herein may enable comparison of two entities in all their relationships. The comparison can be visualized via a browser. The visualization can be enabled by a number of events. In one example, when MDM service 210 identifies potential matches, some of which are candidates for pruning (so that the master data may include a unique and consistent instance of data), the comparison of a potential match with the master data may be visualized to highlight the difference. In another example, a user, such as a consulting analyst may choose to update an otherwise unique record instance. The updates can be visualized as a comparison fin the consulting analyst to approve or reject.

Figure 3:
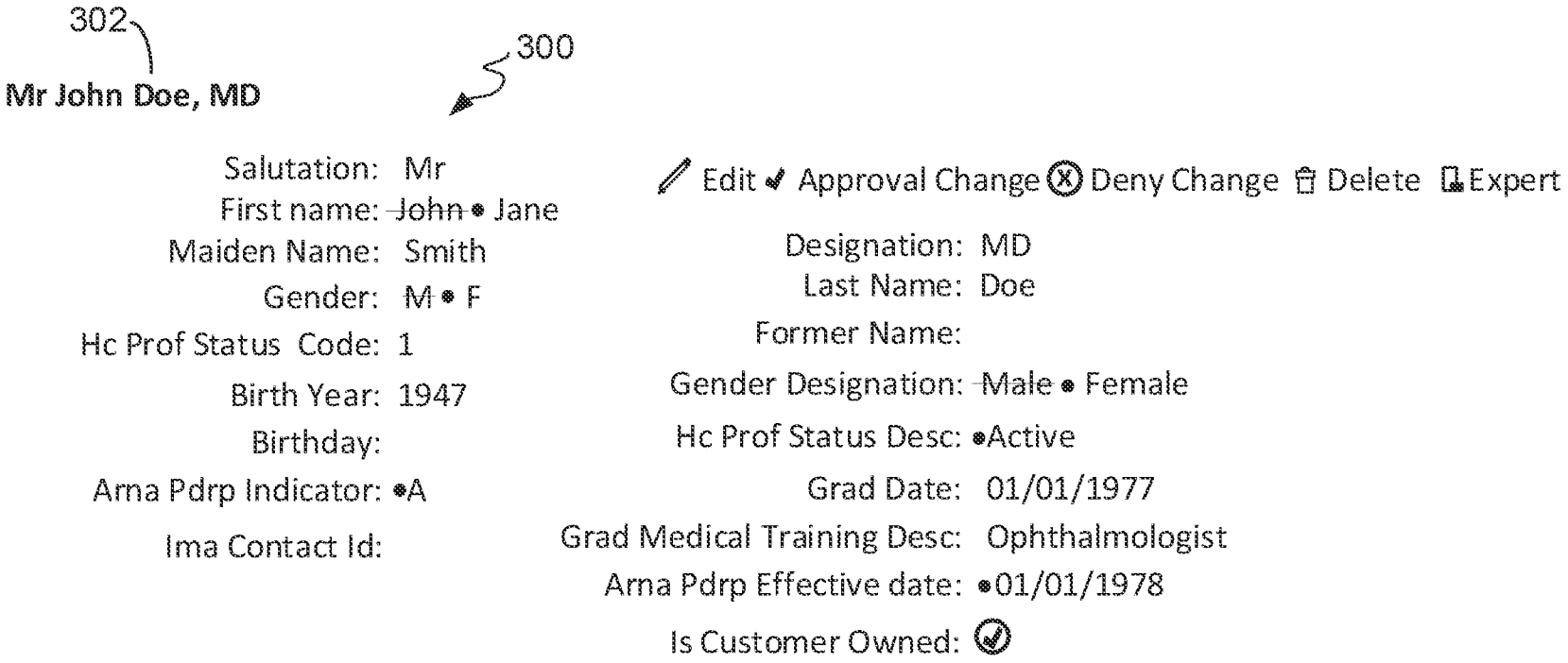
FIG. 3 shows a screen shot of a difference view according to some implementations.

FIG. 3 is an example screen shot 300 showing a comparison of two record instances. The example shows the record of a doctor John Doe 302 being compare with the record of a doctor Jane Doe. The comparison highlights the differences in the attributes of first name, gender, as well as professional status description, indicator, and effective dates. The record of doctor Jane Doe also includes a maiden name. As noted above, the difference view may be displayed when a change is being requested to enter the master data of a record. The visualization serializes the changed-entity in the corresponding old and new-state. Here, serialization means encapsulation of the changed-data as a snapshot so data-stewards can inspect what has transpired to the data.

In the discussed examples, every change made to master data will be stored in a persistent store at a field level with a DateTime stamp. The DateTime stamp may originate from a network time protocol (NTP) server. The NTP server may enforce an authenticity of the time stamp issued (for example, via public key infrastructure). The DateTime stamp may provide a log to track the changes to a certain attribute of an entity. The log may be replayed to enable a reconstruction of all events that have transpired. The log may also be played back to revert an attribute to an earlier state.

Figure 4:
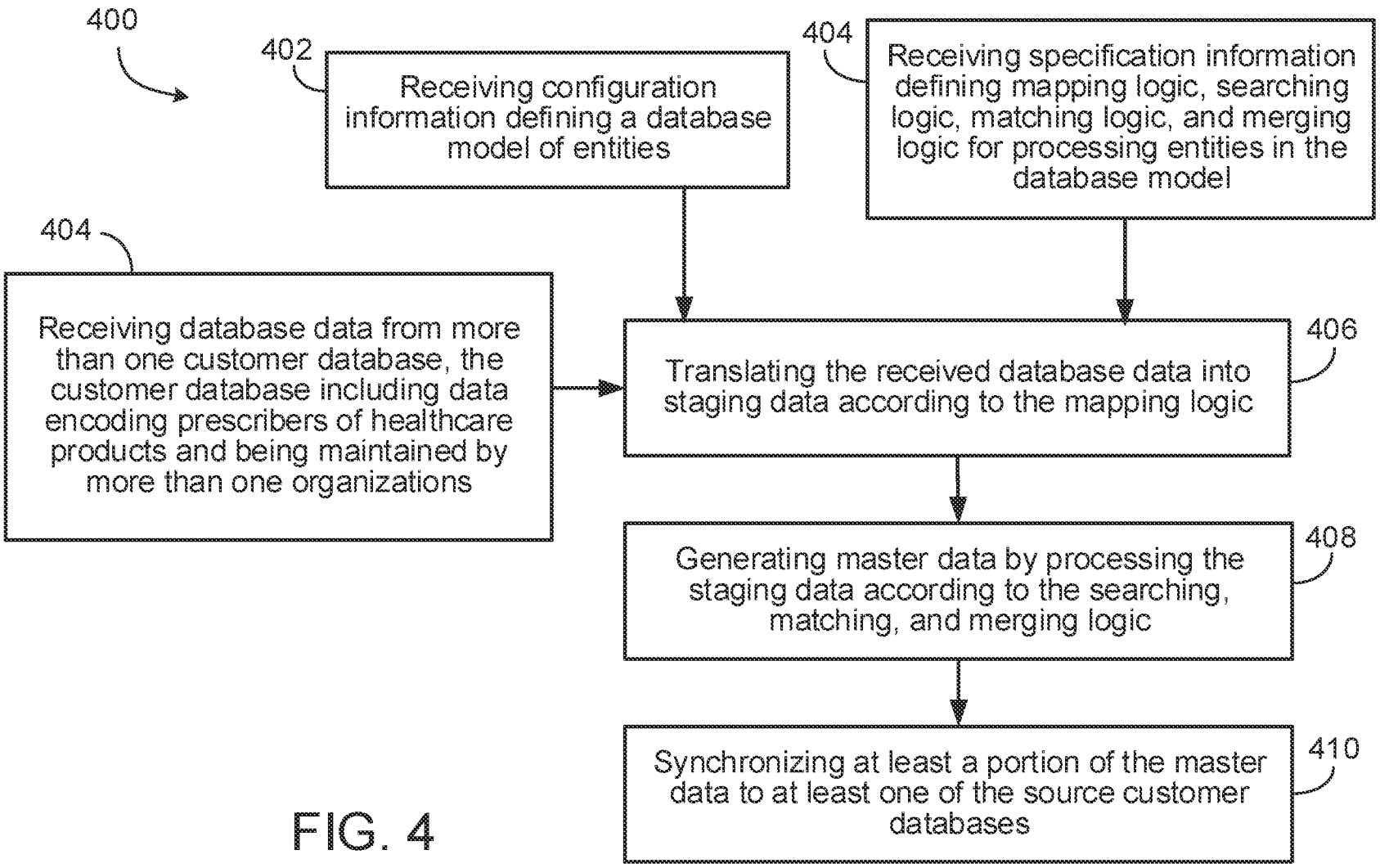
FIG. 4 is flow chart of an example process of managing master data from disparate sources.

FIG. 4 is a flow chart of an example master data management process 400. Initially database information and configuration information are received. In particular, configuration information defining a database model of entities may be provided by an analyst. The database model may include definitions of base entities and related entities. A base entity may define a base class. Each base entity may include one or more related entities. A related entity may include attributes for a base class. Related entities usually have many-to-one relationship with base entities. The configuration information defining the database model may be received at a server computer (402).

Likewise, specification information defining mapping logic, searching logic, matching logic, and merging logic for processing entities defined in the database model may be provided by the analyst. This specification may also be received at the server computer (404).

In addition, database data from more than one source customer databases may be received at the server computer (404). The source customer database may include data encoding prescribers of healthcare products. Each source customer database may be maintained by a separate organization. Hence, the source customer databases may be maintained by different organizations. A ETL layer may then translate the database data from various source customer databases into staging data on the server computer according to the mapping logic (406).

Thereafter, the server computer may generate master data by processing the staging data according to the searching, matching, and merging logic in the receive specification information (408).

Figure 5A:
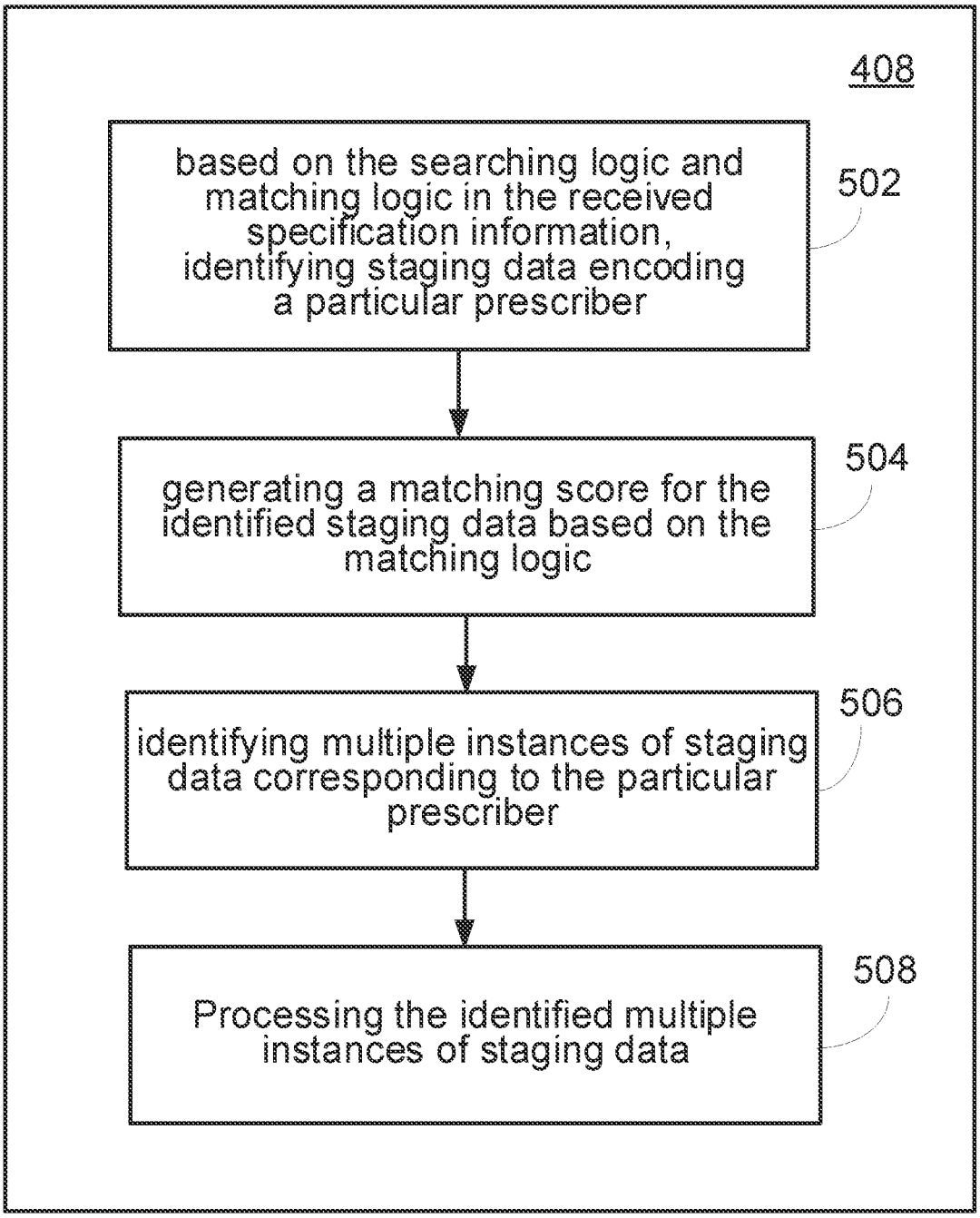
FIGS. 5A and 5B show further details of the example process of managing master data shown in FIG. 4.

Referring to FIG. 5A, based on the searching logic and matching logic in the received specification information, the server computer may identify staging data encoding a particular prescriber (502). The server computer may then generate a matching score for the identified staging data based on the matching logic (504). The matching score may be based on contributions of all matching attributes of an entity. The server computer may also identify multiple instances of staging data corresponding to a particular prescriber (506). The multiple instances of staging data may be processed to prune duplicates while keeping a unique copy (508).

Figure 5B:
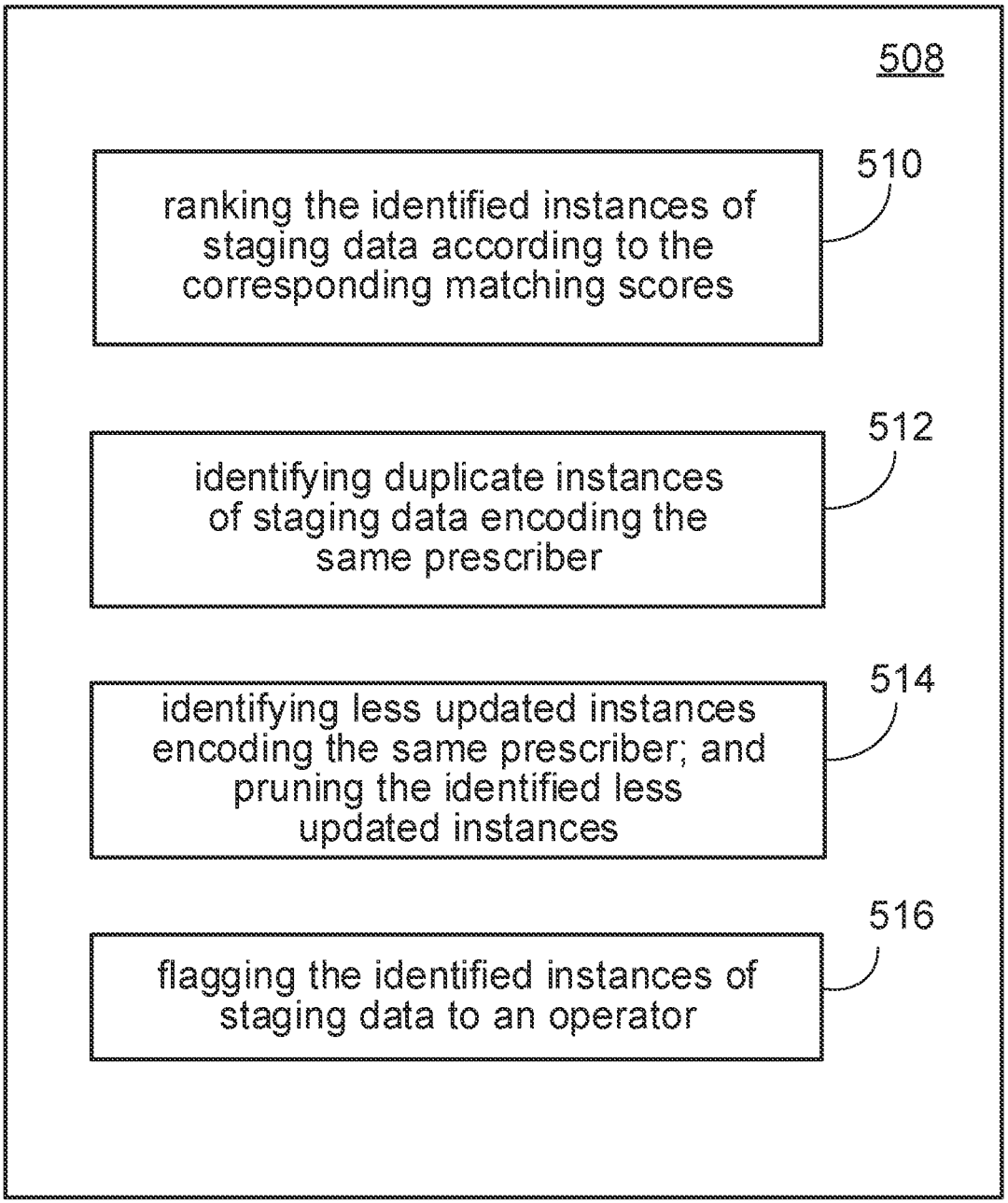

Referring to FIG. 5B, the processing may include ranking the identified instances of staging data according to the corresponding matching scores (510). A higher matching score may indicate a better data quality of the particular instance of staging data. The processing may also include identifying duplicate instances of staging data encoding the same prescriber (512). For the identified duplicate instances of the same prescriber, the server computer may identify less updated instances encoding the same prescriber; and prune the identified less updated instances (514). In some instances, the server computer may flag the identified instances of staging data to an operator (516). The operator may then choose to prune instances of inferior quality (e.g., stale instances). Some implementations may provide a difference view user interface, as illustrated earlier in FIG. 3, for the operator to compare and choose.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data front or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any term or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

[1. A computer-assisted method for master data management, the method comprising:

receiving configuration information encoding a model that defines base entities and related entities, each base entity representing a prescriber of one or more healthcare products, each related entity encoded to include attributes of a base entity;

receiving specification information defining mapping logic, searching logic, matching logic, and merging logic for processing base entities and related entities of the model;

receiving data from more than one source customer databases, the source customer databases including data encoding prescribers of healthcare products and being maintained by more than one organizations;

translating the received data into staging data according to the mapping logic in the received specification information by incorporating the received mapping logic into an extraction, transformation, and loading (ETL) layer between the more than one source customer databases and the staging data such that database data from the more than one source customer databases are automatically transferred via a secure file transfer process after having been converted to staging data in a manner that maps at least one related entity via a many to one mapping to related base entities;

based on the received configuration information and the received specification information, generating a master data schema that specifies the base entities as well as mapping and merging logic to relate the base entities by virtue of the related entities;

generating master data by processing the staging data according to the searching logic, matching logic, and merging logic in the received specification information such that base entities under the master data schema are matched according to the matching logic and the matched base entities are subsequently merged according to the merging logic; and publishing the master data schema to cause at least a portion of the master data to be synchronized through the ETL layer at the source customer databases such that when data in a first source customer database is updated, a second source customer database, different from the first source customer database, is automatically synchronized in accordance with the master data schema, wherein both the first and the second source customer databases encode information from entities that have been mapped under the many-to-one mapping.]

[2. The method of claim 1, wherein processing the staging data comprises:

based on the searching logic and matching logic in the received specification information, identifying staging data that encodes a particular prescriber.]

[3. The method of claim 2, wherein identifying staging data that encodes the prescriber further comprises:

generating a matching score for the identified staging data based on the matching logic.]

[4. The method of claim 3, wherein generating a matching score further comprises:

weighing and combining contributions of matching attributes of the prescriber as encoded by the identified staging data.]

[5. The method of claim 3, wherein identifying staging data encoding the prescriber, further comprises:

identifying multiple instances of staging data corresponding to the particular prescriber.]

[6. The method of claim 5, further comprising:

ranking the identified instances of staging data according to the corresponding matching scores.]

[7. The method of claim 5, further comprising:

identifying duplicate instances of staging data encoding the same prescriber.]

[8. The method of claim 5, further comprising:

identifying less updated instances encoding the same prescriber; and pruning the identified less updated instances.]

[9. The method of claim 5, wherein processing the staging data further comprises:

flagging the identified instances of staging data to an operator.]

[10. method of claim 9, further comprising:

receiving operator feedback to prune an identified instance.]

[11. The method of claim 9, further comprising:

receiving operator feedback that chooses an identified instance as a unique instance encoding the particular prescriber.]

[12. The method of claim 1, wherein publishing to cause at least a portion of the master data to be synchronized includes publishing to cause at least a portion of the master data to be synchronized to a source customer database for which the generated master data includes data encoding a prescriber that is inconsistent with data in the source customer database that encodes the same prescriber.]

[13. The method of claim 1, wherein translating the data into staging data comprises:

converting data encoding a prescriber of healthcare products from one entity in a customer database to another entity under the received data model.]

[14. The method of claim 1, further comprising:

receiving configuration information in an extendable mark-up language.]

[15. The method of claim 1, wherein receiving data comprises: receiving data from a customer relationship management (CRM) database.]

[16. The method of claim 1, wherein receiving data comprises: receiving data from an enterprise relationship management (ERM) database.]

[17. A computer system comprising a processor and at least one memory, the processor is configured to perform the operations of:

receiving configuration information encoding a model that defines base entities and related entities, each base entity representing a prescriber of one or more healthcare products, each related entity encoded to include attributes of a base entity;

receiving configuration information encoding a model that defines base entities and related entities, each base entity representing a prescriber of one or more healthcare products, each related entity encoded to include attributes of a base entity;

receiving specification information defining mapping logic, searching logic, matching logic, and merging logic for processing base entities and related entities of the model;

receiving data from more than one source customer databases, the source customer databases including data encoding prescribers of healthcare products and being maintained by more than one organizations;

translating the received data into staging data according to the mapping logic in the received specification information by incorporating the received mapping logic into an extraction, transformation, and loading (ETL) layer between the more than one source customer databases and the staging data such that database data from the more than one source customer databases are automatically transferred via a secure file transfer process after having been converted to staging data in a manner that maps at least one related entity via a many to one mapping to related base entities;

based on the received configuration information and the received specification information, generating a master data schema that specifies the base entities as well as mapping and merging logic to relate the base entities by virtue of the related entities;

generating master data by processing the staging data according to the searching logic, matching logic, and merging logic in the received specification information such that base entities under the master data schema are matched according to the matching logic and the matched base entities are subsequently merged according to the merging logic; and publishing the master data schema to cause at least a portion of the master data to be synchronized through the ETL layer at the source customer databases such that when data in a first source customer database is updated, a second source customer database, different from the first source customer database, is automatically synchronized in accordance with the master data schema, wherein both the first and the second source customer databases encode information from entities that have been mapped under the many-to-one mapping.]

[18. The computer system of claim 17, wherein processing the staging data comprises:

based on the searching logic and matching logic in the received specification information, identifying staging data encoding a prescriber.]

[19. The computer system of claim 17, wherein publishing to cause at least a portion of the master data to be synchronized includes publishing to cause at least a portion of the master data to be synchronized to a customer database for which the generated master data includes data encoding a prescriber that is inconsistent with data in the customer database that encodes the same prescriber.]

[20. The computer system of claim 17, wherein translating the data into staging data comprises: incorporating the received mapping logic into an extraction, transformation, and loading (ETL) layer between the more than one customer database and the staging data.]

[21. The computer system of claim 17, wherein translating the data into staging data comprises: converting data encoding a prescriber of healthcare products from one entity in a customer database to another entity under the received data model.]

[22. The computer system of claim 17, further comprising:

receiving configuration information in an extendable mark-up language.]

[23. The computer system of claim 17, wherein receiving data comprises: receiving data from a customer relationship management (CRM) database.]

[24. The computer system of claim 17, wherein receiving data comprises: receiving data from an enterprise relationship management (ERM) database.]

[25. A non-transitory computer-readable medium comprising software instructions that, when executed by a processor of a computer, cause the processor to perform the operations of:

receiving configuration information encoding a model that defines base entities and related entities, each base entity representing a prescriber of one or more healthcare products, each related entity encoded to include attributes of a base entity;

receiving specification information defining mapping logic, searching logic, matching logic, and merging logic for processing base entities and related entities of the model;

receiving data from more than one source customer databases, the source customer databases including data encoding prescribers of healthcare products and being maintained by more than one organizations;

translating the received data into staging data according to the mapping logic in the received specification information by incorporating the received mapping logic into an extraction, transformation, and loading (ETL) layer between the more than one source customer databases and the staging data such that database data from the more than one source customer databases are automatically transferred via a secure file transfer process after having been converted to staging data in a manner that maps at least one related entity via a many to one mapping to related base entities;

based on the received configuration information and the received specification information, generating a master data schema that specifies the base entities as well as mapping and merging logic to relate the base entities by virtue of the related entities;

generating master data by processing the staging data according to the searching logic, matching logic, and merging logic in the received specification information such that base entities under the master data schema are matched according to the matching logic and the matched base entities are subsequently merged according to the merging logic; and publishing the master data schema to cause at least a portion of the master data to be synchronized through the ETL layer at the source customer databases such that when data in a first source customer database is updated, a second source customer database, different from the first source customer database, is automatically synchronized in accordance with the master data schema, wherein both the first and the second source customer databases encode information from entities that have been mapped under the many-to-one mapping.]

*26. A method comprising:*

*translating source data into staging data based on a set of mapping logic, wherein the staging data is based on a data model that defines a set of base entities and a set of related entities for each of the set of base entities, each base entity in the set of base entities representing a prescriber in a set of prescribers and each related entity comprising an attribute of a corresponding prescriber;*

*loading the staging data into a master account database, wherein the set of mapping logic is incorporated into an extraction, transformation, and loading (ETL) layer between a plurality of source customer databases where the source data is hosted and the master account database;*

*generating, from the staging data, master data based at least in part on a set of search logic, a set of match logic, and a set of merge logic;*

*generating, from the staging data, a master data schema based at least in part on the set of search logic, the set of match logic, and the set of merge logic, the master data schema to relate base entities among the set of base entities based on their corresponding related entities; and*

*synchronizing, through the ETL layer, the master data across the plurality of source customer databases, such that when data in a first source customer database of the plurality of source customer databases is updated, a second source customer database of the plurality of source customer databases is automatically synchronized in accordance with the master data schema.*

*27. The method of claim 26, wherein generating the master data comprises: identifying one or more base entities of the staging data that each represent a particular prescriber based on the searching logic and matching logic.*

*28. The method of claim 27, wherein identifying the one or more base entities of the staging data that each represent the particular prescriber comprises:*

*generating a match score for each of the set of base entities based on the set of matching logic, wherein base entities that have a match score that exceeds a threshold represent the particular prescriber.*

*29. The method of claim 28, wherein generating a matching score for a base entity of the set of base entities comprises:*

*weighing and combining related entities of the base entity that match attributes of a master entity representing the particular prescriber, the master entity stored in the master account database.*

*30. The method of claim 29, further comprising:*

*identifying, from among base entities that do not have a match score above the threshold, one or more base entities that potentially represent the particular prescriber; and*

*persisting base entities that do not have a match score above the threshold and do not potentially represent the particular prescriber as unique entities in the master account database.*

*31. The method of claim 30, further comprising:*

*for each of the one or more base entities that potentially represent the particular prescriber, determining whether to merge the base entity into the master entity based on the set of merge logic.*

*32. The method of claim 29, further comprising:*

*for each of the one or more base entities that represent the particular prescriber:*

*determining whether the base entity is less updated than the master entity; and*

*pruning the base entity if it is less updated than the master entity, and merging the base entity into the master entity if it is more updated than the master entity.*

*33. A system comprising:*

*a memory; and*

*one or more processors operatively coupled to the memory, the memory storing instructions that, when executed by the one or more processors, cause the one or more processors to:*

*translate source data into staging data based on a set of mapping logic, wherein the staging data is based on a data model that defines a set of base entities and a set of related entities for each of the set of base entities, each base entity in the set of base entities representing a prescriber in a set of prescribers and each related entity comprising an attribute of a corresponding prescriber;*

*load the staging data into a master account database, wherein the set of mapping logic is incorporated into an extraction, transformation, and loading (ETL) layer between a plurality of source customer databases where the source data is hosted and the master account database;*

*generate, from the staging data, master data based at least in part on a set of search logic, a set of match logic, and a set of merge logic;*

*generate, from the set of staging data, a master data schema based at least in part on the set of search logic, the set of match logic, and the set of merge logic, the master data schema to relate base entities among the set of base entities by virtue of their corresponding related entities; and*

*synchronize, through the ETL layer, the master data across the plurality of source customer databases, such*

*that when data in a first source customer database of the plurality of source customer databases is updated, a second source customer database of the plurality of source customer databases is automatically synchronized in accordance with the master data schema.*

*34. The system of claim 33, wherein to generating the master data comprises:*

*identifying one or more base entities of the staging data that each represent a particular prescriber based on the searching logic and matching logic.*

*35. The system of claim 34, wherein identifying the one or more base entities of the staging data that each represent the particular prescriber comprises:*

*generating a match score for each of the set of base entities based on the set of matching logic, wherein base entities that have a match score that exceeds a threshold represent the particular prescriber.*

*36. The system of claim 35, wherein generating a matching score for a base entity of the set of base entities comprises:*

*weighing and combining related entities of the base entity that match attributes of a master entity representing the particular prescriber, the master entity stored in the master account database.*

*37. The system of claim 36, wherein the instructions, when executed, cause the one or more processors to:*

*identify, from among base entities that do not have a match score above the threshold, one or more base entities that potentially represent the particular prescriber; and*

*persist base entities that do not have a match score above the threshold and do not potentially represent the particular prescriber as unique entities in the master account database.*

*38. The system of claim 37, wherein the instructions, when executed, cause the one or more processors to:*

*for each of the one or more base entities that potentially represent the particular prescriber, determine whether to merge the base entity into the master entity based on the set of merge logic.*

*39. The system of claim 36, wherein the instructions, when executed, cause the one or more processors to:*

*for each of the one or more base entities that represent the particular prescriber:*

*determine whether the base entity is less updated than the master entity; and*

*prune the base entity if it is less updated than the master entity, and merge the base entity into the master entity if it is more updated than the master entity.*

*40. A non-transitory computer-readable medium having instructions stored thereon which, when executed by one or more processors, cause the one or more processors to:*

*translate source data into staging data based on a set of mapping logic, wherein the staging data is based on a data model that defines a set of base entities and a set of related entities for each of the set of base entities, each base entity in the set of base entities representing a prescriber in a set of prescribers and each related entity comprising an attribute of a corresponding prescriber;*

*load the staging data into a master account database, wherein the set of mapping logic is incorporated into an extraction, transformation, and loading (ETL) layer between a plurality of source customer databases where the source data is hosted and the master account database;*

*generate, from the staging data, master data based at least in part on a set of search logic, a set of match logic, and a set of merge logic;*

*generate, from the set of staging data, a master data schema based at least in part on the set of search logic, the set of match logic, and the set of merge logic, the master data schema to relate base entities among the set of base entities by virtue of their corresponding related entities; and*

*synchronize, through the ETL layer, the master data across the plurality of source customer databases, such that when data in a first source customer database of the plurality of source customer databases is updated, a second source customer database of the plurality of source customer databases is automatically synchronized in accordance with the master data schema.*

*41. The system of claim 40, wherein generating the master data comprises:*

*identifying one or more base entities of the staging data that each represent a particular prescriber based on the searching logic and matching logic.*

*42. The system of claim 41, wherein identifying the one or more base entities of the staging data that each represent the particular prescriber comprises:*

*generating a match score for each of the set of base entities based on the set of matching logic, wherein base entities that have a match score that exceeds a threshold represent the particular prescriber.*

*43. The system of claim 42, wherein generating a matching score for a base entity of the set of base entities comprises:*

*weigh and combine related entities of the base entity that match attributes of a master entity representing the particular prescriber, the master entity stored in the master account database.*

*44. The system of claim 43, wherein the instructions, when executed, cause the one or more processors to:*

*identify, from among base entities that do not have a match score above the threshold, one or more base entities that potentially represent the particular prescriber; and*

*persist base entities that do not have a match score above the threshold and do not potentially represent the particular prescriber as unique entities in the master account database.*

*45. The system of claim 44, wherein the instructions, when executed, cause the one or more processors to: for each of the one or more base entities that potentially represent the particular prescriber, determine whether to merge the base entity into the master entity based on the set of merge logic.*

*46. The system of claim 43, wherein the instructions, when executed, cause the one or more processors to:*

*for each of the one or more base entities that represent the particular prescriber:*

*determine whether the base entity is less updated than the master entity; and*

*prune the base entity if it is less updated than the master entity, and merge the base entity into the master entity if it is more updated than the master entity.*

* * * * *